United States Patent [19]

Webb

[11] Patent Number: 4,584,388

[45] Date of Patent: Apr. 22, 1986

[54] METHOD AND COMPOSITION FOR PREPARING AROMATIC POLYCARBOXYLIC ACIDS AND THEIR ANHYDRIDES FROM POLYCARBOXIMIDES

[75] Inventor: Jimmy L. Webb, Ballston Lake, N.Y.

[73] Assignee: General Electric Company, Schenectady, N.Y.

[21] Appl. No.: 691,292

[22] Filed: Jan. 14, 1985

[51] Int. Cl.[4] .................... C07D 307/89; C07C 63/00
[52] U.S. Cl. .................................. 549/241; 562/429; 562/432; 562/460; 562/473
[58] Field of Search ................ 549/241; 562/429, 432, 562/460, 473

[56] References Cited

U.S. PATENT DOCUMENTS 4,116,980  9/1978  Webb ................................ 549/241
4,329,292  5/1982  Webb ................................ 549/241

Primary Examiner—Richard L. Raymond
Attorney, Agent, or Firm—William H. Pittman; James C. Davis, Jr.; James Magee, Jr.

[57] ABSTRACT

Aromatic polycarboxylic acids and their anhydrides such as bisphenol A dianhydride are prepared from the corresponding polycarboximides, such as bisphenol A bisimide, by an exchange reaction with phthalic acid or phthalic anhydride and water in the presence of dimethyl-n-butylamine as an exchange catalyst. The use of this amine results in the formation of a product of decreased color, as compared with the use of triethylamine.

9 Claims, 9 Drawing Figures (I) 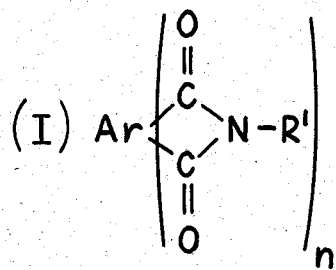 (II) 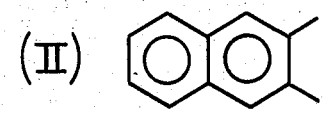
(III) 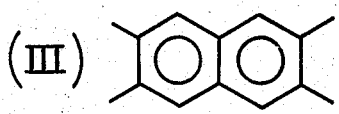 (IV) 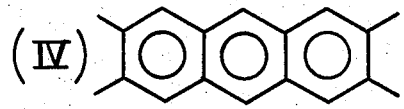
(V) 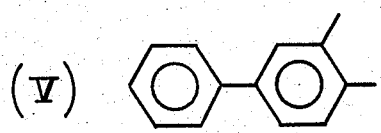 (VI) 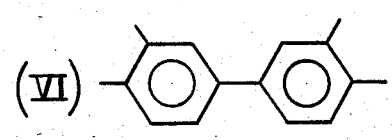
(VII) 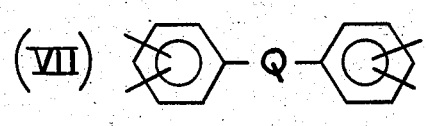 (VIII) 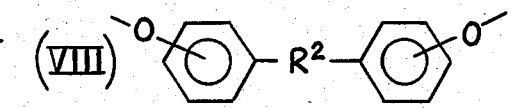
(XI) 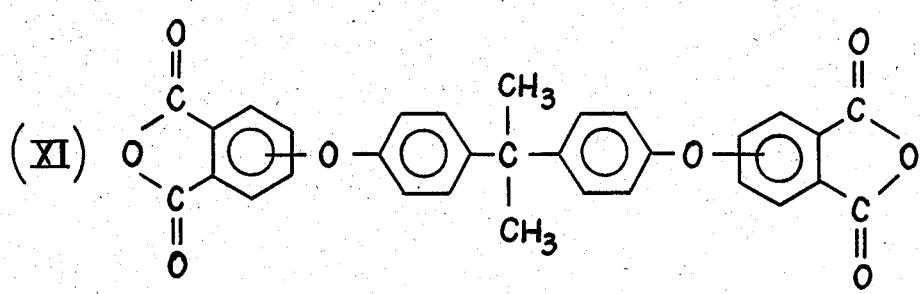

METHOD AND COMPOSITION FOR PREPARING AROMATIC POLYCARBOXYLIC ACIDS AND THEIR ANHYDRIDES FROM POLYCARBOXIMIDES

This invention relates to the preparation of aromatic polycarboxylic acids and their anhydrides from the corresponding polycarboximides. More particularly, it relates to the preparation of such anhydrides by an exchange reaction in the presence of an exchange catalyst, and reactive compositions used in such preparation.

Aromatic polycarboxylic acids and their anhydrides may be prepared by an exchange reaction between a corresponding aromatic N-substituted polycarboximide, wherein the N-substituent may be an alkyl or aryl radical, a mixture of phthalic acid or phthalic anhydride and water. This reaction is particularly useful for the preparation of aromatic ether bis(phthalic acids) or (phthalic anhydrides), especially 2,2-bis[4-(3,4-dicarboxyphenoxy)phenyl]propane dianhydride (hereinafter "bisphenol A dianhydride"), as disclosed in the following U.S. Pat. Nos. the disclosures of which are incorporated by reference herein:
  4,116,980
  4,128,574
  4,318,857
  4,329,291
  4,329,292
  4,329,496
  4,340,545.

According to several of these patents, the reaction is conveniently conducted in the presence of an exchange catalyst, particularly a trialkylamine such as trimethylamine, triethylamine, tripropylamine or tributylamine. Aromatic dianhydrides produced by this method are useful in the preparation of polyimides by reaction with diamines. In particular, bisphenol A dianhydride is used in the preparation of valuable polyetherimides.

It is well known that polymers such as polyetherimides are most desirably colorless or very light-colored. Thus, a disadvantage in the use of such tertiary amines as triethylamine in the exchange reaction is the formation of highly colored by-products which remain in the dianhydride during polyetherimide formation, thus discoloring the polymeric product. It has been found that many of these colored by-products are formed by degradation of triethylamine.

A principal object of the present invention, therefore, is to provide an improved method for the preparation of aromatic polycarboxylic acids and anhydrides.

A further method is to provide a method for the preparation of such compounds by a tertiary aminecatalyzed exchange reaction between a corresponding polycarboximide and phthalic acid or phthalic anhydride, and reactive compositions suitable for use in said method.

A still further object is to prepare such compounds by a catalytic method in which the catalyst does not contribute materially to discoloration of polymeric products prepared from the anhydrides.

Other objects will in part be obvious and will in part appear hereinafter.

In its broadest sense, the present invention is an improvement in a method for preparing an aromatic polycarboxylic acid or anhydride thereof by an exchange reaction, in the presence of an exchange catalyst, between phthalic acid or phthalic anhydride, water and least one aromatic polycarboximide having formula I in the drawings, wherein Ar is an aromatic radical, $R^1$ is a $C_{1-8}$ alkyl radical or a $C_{6-20}$ aromatic hydrocarbon or halogenated aromatic hydrocarbon radical, n is 1 or 2 and the carbonyl groups in a single imide radical are attached to Ar at ortho- positions. Said improvement comprises using dimethyl-n-butylamine as the exchange catalyst.

The method of this invention is applicable to the preparation of various aromatic polycarboxylic acids and their anhydrides, especially dicarboxylic acid monoanhydrides and tetracarboxylic acid dianhydrides, from the corresponding polycarboximides. (As used herein, the term "polycarboximide" designates an imide of a polycarboxylic acid; it may contain one or more than one imide group.) In general, the Ar value may be any aromatic radical containing one or two sets of free ortho-positions to accommodate one or two imide groups, with the sole exception of phthalimides (since phthalic acid or phthalic anhydride is another of the reactants). Formulas II–VI are examples of suitable Ar radicals.

The preferred Ar radicals are represented by formula VII, wherein Q is a bridging radical and the free valence bonds in each aromatic rin are in the 2,3- or 3,4-positions or both with respect to Q. (They are usually both in the 3,4-positions.) The Q value therein may be selected from a wide variety of bridging radicals including oxygen atoms, sulfur atoms and divalent groups such as methylene, ethylene, propylidene, carbonyl, sulfone and the like. More preferably, Q has formula VIII, wherein $R^2$ is a $C_{1-4}$ alkylene radical and especially the isopropylidene radical. The oxygen atoms are most often both in the 4-positions (i.e., the para-positions) with respect to $R^2$.

The $R^1$ value may be, for example, methyl, ethyl, n-hexyl, phenyl, 1-naphthyl, 2-naphthyl, p-chlorophenyl or m-tolyl. It is usually methyl or phenyl and preferably methyl.

As will be apparent from the above-expressed preferences, the present invention is particularly useful for the preparation of the aromatic ether dianhydrides represented by formula XI. These include especially the aforementioned bisphenol A dianhydride and its symmetrical position isomer, 2,2-dimethyl-[4-(2,3-dicarboxyphenoxy)phenyl]propane dianhydride.

The details of the exchange reaction, other than the identity of the catalyst, are adequately disclosed in the aforementioned U.S. patents and need not be repeated in detail here. They generally involve the reaction of a bisimide containing an alkyl or aryl N-substituent, preferably a $C_{1-4}$ alkyl substituent and most preferably methyl, with an aqueous solution of phthalic acid or phthalic anhydride. The bisimide is most often 2,2-bis[4-(3,4-dicarboxyphenoxy)phenyl]propane bis-N-methylimide (hereinafter "bisphenol A bisimide") and the resulting product bisphenol A dianhydride. Therefore, frequent reference will be made to these compounds hereinafter. It should be understood, however, that other imides may be substituted for bisphenol A bisimide when appropriate.

The bisimide may be dissolved in a substantially inert organic solvent, although solvent-free methods are also within the scope of the invention. Suitable solvents are water-immiscible liquids which are good solvents for the imides, whether reactants or products. Illustrative solvents are aromatic liquids such as benzene, toluene, xylene, chlorobenzene and o-dichlorobenzene, with toluene being preferred. The reaction is frequently conducted under pressure, typically about 200–700 psi., and at a temperature within the range of about 150°–300° C.

The equilibrium may be shifted to the right by removal of the N-methylphthalimide by-product. This may be accomplished by such means as solvent extraction or venting the pressurized reaction vessel several times to the atmosphere, whereupon an aqueous phase rich in N-methylphthalimide and containing relatively insignificant amounts of phthalic acid is removed.

The ratio of equivalents of phthalic acid or anhydride to bisphenol A bisimide is generally within the range of about 0.5–40:1 and preferably about 1–10:1, and the corresponding ratio of water to bisphenol A bisimide is usually about 0.1–1500:1 and preferably about 50–200:1. For the purposes of this invention, the equivalent weight of water is equal to its molecular weight and the equivalent weight of an anhydride or bisimide is its molecular weight divided by the number of intramolecular anhydride or bisimide groups therein.

The present invention is based on the discovery that the use of dimethyl-n-butylamine as the exchange catalyst results in the formation of a product which has a much lighter color than those obtained by the use of other amines such as triethylamine. This lighter color carries over into polyimide prepared from the dianhydride. The substitution of dimethyl-n-butylamine for triethylamine, a commonly used exchange catalyst, requires substantially no design changes in the equipment or process, since the two have the same molecular weight and differ in boiling point by only 2° C. The invention also includes reactive compositions comprising phthalic acid or phthalic anhydride, water, at least one aromatic polycarboximide as described hereinabove, and dimethyl-n-butylamine.

Acording to the invention, dimethyl-n-butylamine is incorporated in the reaction mixture in an amount to provide about 1–15 and preferably about 3–8 equivalents per equivalent of bisphenol A bisimide. (The equivalent weight of dimethyl-n-butylamine is equal to its molecular weight.)

The method of this invention is illustrated by an example in which 59.3 parts by weight (0.216 equivalent) of bisphenol A bisimide, 107.17 parts (0.645 equivalent) of phthalic acid, 246.18 parts (13.49 equivalents) of water and 85.76 parts (0.85 equivalent) of dimethyl-n-butylamine were combined in an autoclave, which is purged with nitrogen by three successive instances of sealing, pressurizing to 300 psi. and venting. The sealed autoclave was then heated at 170° C. for 3 hours, cooled and opened. Toluene, 433 parts, was added and the mixture was stirred for ½ hour to extract the imide constituents. One hundred parts of the aqueous phase was stripped at 100°–250° C./25 torr.

Color values for the samples were determined by dissolving 500 mg. of the product in 10 ml. of methylene chloride and obtaining the ultraviolet-visible spectrum of the resulting solution. The sum of the absorbance values at 420, 460 and 500 nm. was multiplied by 100 to give a color number which was comparable for various samples.

When this procedure was used to prepare bisphenol A dianhydride from a bisphenol A bisimide sample having a color number of 6.3, duplicate reaction runs yielded samples of bisphenol A dianhydride having color numbers of 28.3 and 27.7. Two control runs, using triethylamine in the same amount as the exchange catalyst, yielded bisphenol A dianhydride products having color numbers of 40.0 and 39.9.

What is claimed is:

1. In a method for preparing an aromatic polycarboxylic acid or anhydride thereof by an exchange reaction, in the presence of an exchange catalyst, between phthalic acid or phthalic anhydride, water and at least one aromatic polycarboximide having the formula

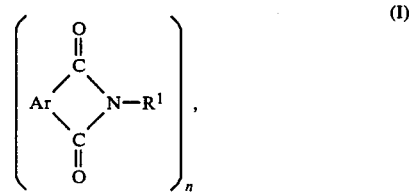

wherein Ar is an aromatic radical, $R^1$ is a $C_{1-8}$ alkyl radical or a $C_{6-20}$ aromatic hydrocarbon or halogenated aromatic hydrocarbon radical, n is 1 or 2 and the carbonyl groups in a single imide radical are attached to Ar at ortho positions, the improvement which comprises using dimethyl-n-butylamine as the exchange catalyst.

2. A method according to claim 1 wherein the polycarboximide is a bisimide in which n is 2.

3. A method according to claim 2 wherein Ar has the formula

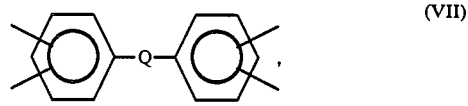

wherein Q is a bridging radical.

4. A method according to claim 3 wherein Q has the formula

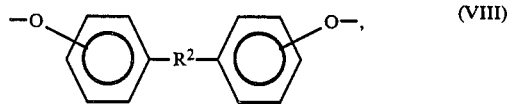

wherein $R^2$ is a $C_{1-4}$ alkylene radical.

5. A method according to claim 4 wherein $R^1$ is methyl or phenyl.

6. A method according to claim 5 wherein about 1–15 equivalents or dimethyl-n-butylamine are used per equivalent of bisimide.

7. A method according to claim 6 wherein $R^2$ is isopropylidene.

8. A method according to claim 7 wherein the ratio of equivalents of phthalic acid or anhydride and water to bisimide are within the range of about 0.5–40:1 and about 0.1–1500:1, respectively.

9. In a method for preparing bisphenol A dianhydride by an exchange reaction, in the presence of an exchange catalyst, between phthalic anhydride, water and bisphenol A bisimide, the ratio of equivalents of phthalic anhydride and water to bisphenol A bisimide being within the range of about 1–10:1 and about 50–200:1, respectively, and said reaction being conducted at a temperature within the range of about 150°–300° C. and at a pressure of about 200–700 psi., the improvement which comprises using dimethyl-n-butylamine as the exchange catalyst, said dimethyl-n-butylamine being present in the amount of about 3–8 equivalents per equivalent of bisimide.

* * * * *